United States Patent [19]

Jongsma

[11] Patent Number: 5,406,342

[45] Date of Patent: Apr. 11, 1995

[54] SYSTEM FOR DETERMINING THE TOPOGRAPHY OF A CURVED SURFACE

[75] Inventor: Franciscus H. M. Jongsma, Ulestraten, Netherlands

[73] Assignee: Euclid Medical Instruments, Maastricht, Netherlands

[21] Appl. No.: 5,244

[22] Filed: Jan. 15, 1993

[30] Foreign Application Priority Data

Jan. 15, 1992 [NL] Netherlands .................. 9200071

[51] Int. Cl.$^6$ ............................................. A61B 3/10
[52] U.S. Cl. ................................. 351/212; 356/376; 351/221
[58] Field of Search ............... 351/200, 205, 211, 212, 351/221; 356/376, 374, 345; 250/237 G

[56] References Cited

U.S. PATENT DOCUMENTS

| | | | |
|---|---|---|---|
| 4,722,600 | 2/1988 | Chiang | 357/374 |
| 5,120,123 | 6/1992 | Akiyama | 351/221 |
| 5,135,308 | 8/1992 | Kuchel | 356/376 |
| 5,135,309 | 8/1992 | Kuchel et al. | 356/376 |

FOREIGN PATENT DOCUMENTS

| | | |
|---|---|---|
| 2254781 | 7/1975 | France . |
| 2292213 | 6/1976 | France . |
| 4007502 | 9/1991 | Germany . |

OTHER PUBLICATIONS

Frobin et al, "Rasterstereography: A Photogrammetric Method for Meassurement of Body Surfaces", Journal of Biological Photography, vol. 51, No. 1 Jan. 1983.
Nouvelle Revue b'optique, vol. 6, No. 2, pp. 67–86, Oct. 1975 for Characterization and Control of Threedimensional Objects Using Fringe Projection.
Spie, Ecoosa for "Real-Time Contouring of Toothimprints", vol. 492, pp. 500–506, by Jongsma et al.
Applied Optics, vol. 18, No. 21, Nov. 1, 1979, for Corneal Topography Using MoiréContour Fringes, by Tetsuo Kawara.

*Primary Examiner*—William L. Sikes
*Assistant Examiner*—Huy Mai
*Attorney, Agent, or Firm*—Bachman & LaPointe

[57] ABSTRACT

A system for determining the topography of a curved surface, comprising a device for projecting patterns of lines on the surface to be examined, which device includes two projectors disposed at an angle relative to each other, each provided with a raster of parallel straight lines, which are positioned at right angles to the plane through the projection axes and a rectangular diaphragm, of which the long sides are parallel to the lines of the raster, and a detection device for registering the image formed on the surface. The system is implemented such that an additive moiré pattern is produced and that a pilot monitor in conjunction with an electronic filter is provided for real-time visualizing this moiré pattern. The detection device is implemented for registering the image without moiré interference, suitable for discrete Fourier analysis. The registration of the formed height line map for proper focussing or for obtaining an end product is electronically filtered, with the object of being able to see highly contrasting moiré height contours in real time on a monitor. The light source for both projectors is a slit shaped continuous light source combined with a slit shaped flashlamp, which—by means of synchronization at the end of the first raster period and the beginning of the second raster period respectively—illuminate a complete TV raster in only a few ms, and in which the half rasters can complement each other afterwards through explicit digital analysis.

8 Claims, 6 Drawing Sheets

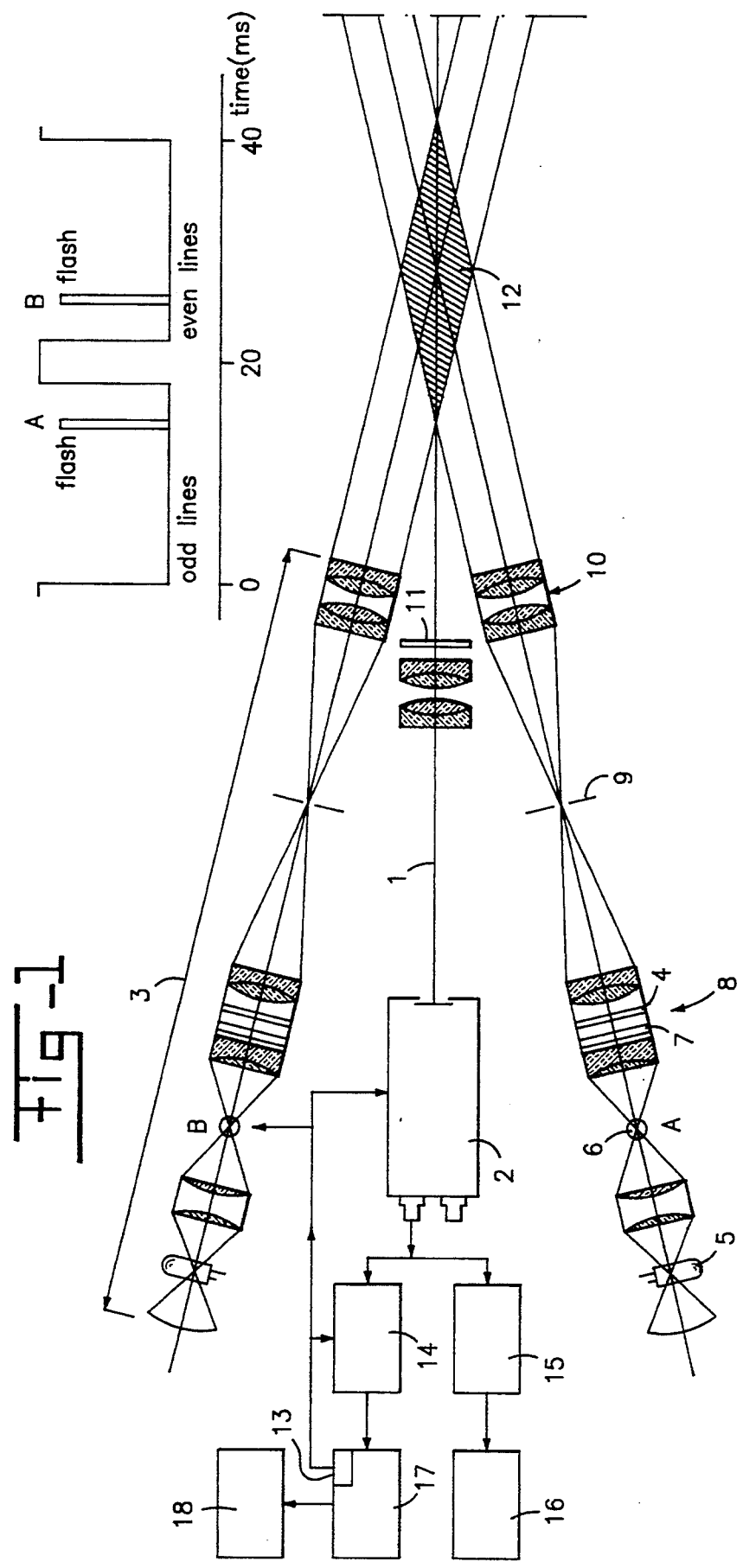

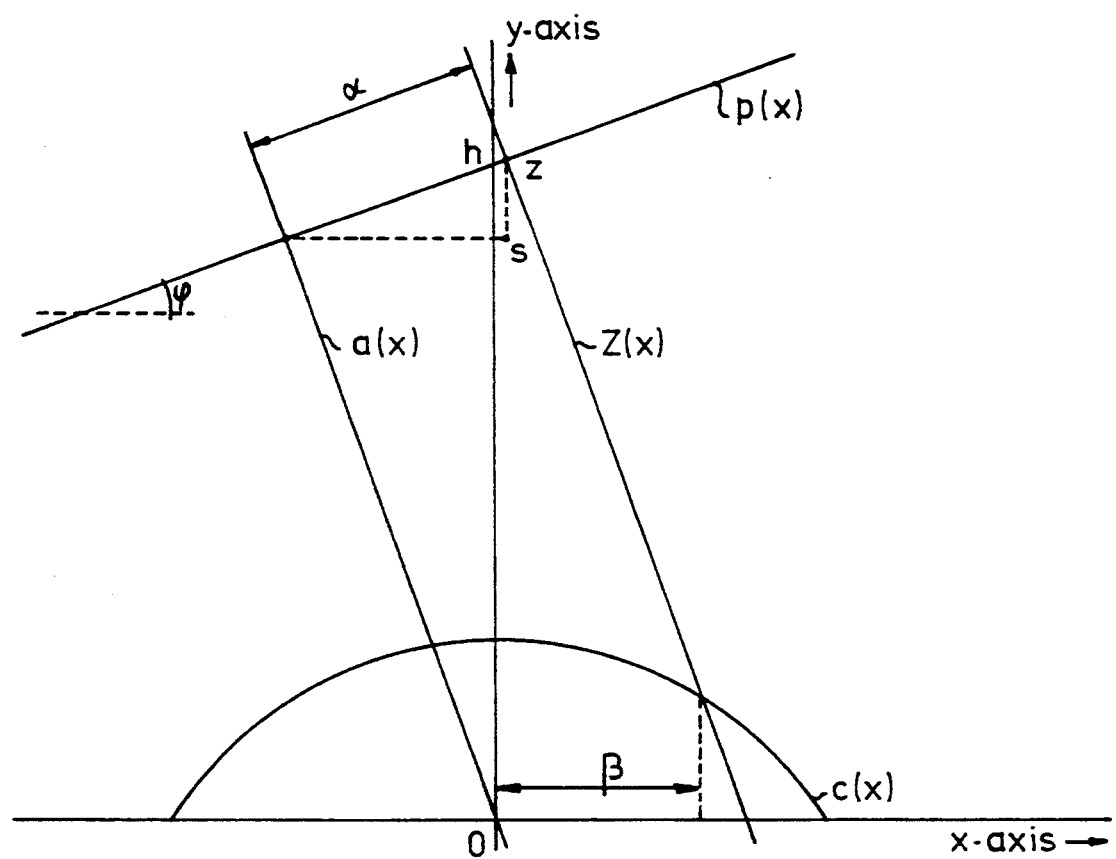

Fig-4
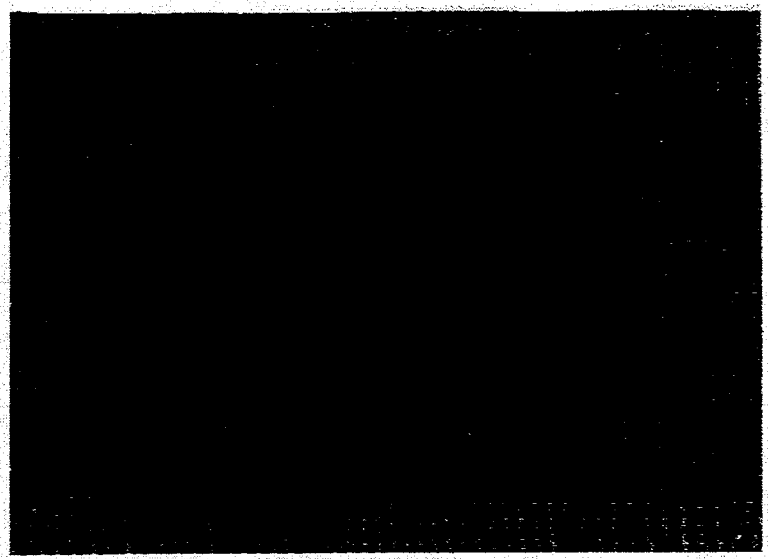
a
b
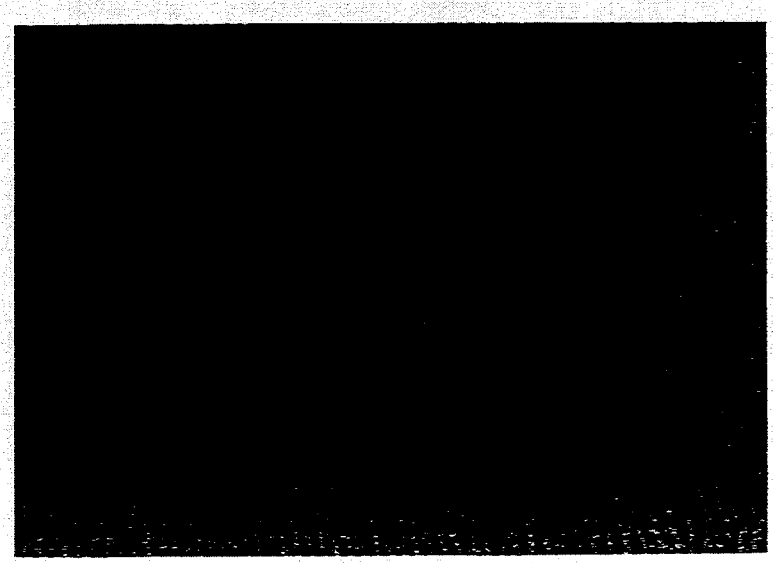
c

SYSTEM FOR DETERMINING THE TOPOGRAPHY OF A CURVED SURFACE

BACKGROUND OF THE INVENTION

The invention relates to a system for determining the topography of a curved surface, comprising a device for projecting patterns of lines on the surface to be examined, a detector device for registration of the image formed on the surface. Such systems are used, inter alia, in the case of the so-called keratometer for determining the external shape of the human eye, in particular the curvature of the external surface of the cornea, for example for measuring for contact lenses and accurately determining the topography of the cornea before and after surgery.

These systems can also be used in manufacturing and checking curved objects.

With the known commercially available photokeratometer the radius of curvature of the cornea is measured locally by comparing mirrored measurement figures on the interface between air and lacrimal fluid with test figures.

Places of equal slope can be mapped in this way. In the interpretation of such registrations, without previous knowledge of the object, errors cannot be ruled out. Only a limited area of the cornea is measured.

Unequivocal registrations of the topography of the surface of the cornea can be obtained with the keratometer of the type which is described in an article by Tetsuo Kawara, "Corneal topography using moiré contour fringes", in Applied Optics, Vol. 18, pp. 3675–3678 (Nov. 1979). Such a keratometer makes use of moiré contour lines, which are lines of equal height. For this purpose, the reflecting surface of the cornea is transformed into a perfectly diffusely radiating surface, through the application of a fluorescein film, as is necessary for said moiré technique. The fluorescent light of the fluorescein film is used to form the image, while the excitation light (which through specular reflection could distort the image) of the projection device, consisting of a single projector, is filtered out. In order to achieve the accuracy for a spherical surface which he claimed, Tetsuo Kawara used a grating with approximately 12 line pairs per millimeter (lp/mm) which, because of a narrow slit-shaped diaphragm in the projection device having optical compensation for the slanting projection angle relative to the viewing axis of the keratometer and a small enough diaphragm of the camera with the required depth of field, forms an image on the reference grating of the camera.

Due to the slanting projection angle, the camera "sees" a superimposed pattern of a projected grating slightly deformed by the convex cornea and the reference grating. The spatial beat between the gratings, which becomes visible as an interference phenomenon, is known as moiré. This interference image represents lines of equal height. Since in this moiré arrangement a multiplication contrast is obtained, the height lines can be read directly from the photographs. Translation of these height lines into three meridional profiles produces information on the local radius of curvature of the cornea.

A serious general limitation of the moiré projection system described is that, on the one hand, sufficient depth of field is required, for which a small diaphragm is needed, while, on the other hand, the height contour interval must be as small as possible, which only a grating with a large number of lp/mm can provide. The system described by Tetsuo Kawara is therefore diffraction limited. A higher resolution can be obtained only at the expense of the depth of field, or by increasing the projection angle of the grating relative to the optical axis of the camera. With a small depth of field the whole cornea is not mapped in one exposure, and a larger projection angle than approximately 18° produces an image which can no longer be interpreted visually, on account of the occurrence of optical artifacts. In the case of the instrument described the height lines are displayed at the position of the reference grating instead of being located on the surface to be registered, which means that the flexibility of the instrument with regard to variation of image scale and image angle is low. The sign of the slope is not known (from previous knowledge is derived as "convex"). The product of Tetsuo Kawara's keratometer is a photograph. The translation of the height lines thus recorded into local radius of curvature, eccentricity etc. has to be carried out from there.

The dependence on very fine gratings in order to keep the moiré contour interval (=measuring point) limited, could be removed in principle if, instead of the intensity distribution of the moiré image, the local phase of the projected grating were used as the measuring point.

Moiré height lines of a surface of an object are formed by the relative phases between the projected grating and the reference grating. The height lines will shift due to shifting of one of the gratings, with the result that a continuous phase measurement at one measuring point is possible. The intensity variation is then a measure of the phase variation. The measuring sensitivity and the accuracy then increase greatly. Since the movement device of the moving grating is known, the sign of the slope can be determined. In the case of the keratometer, on account of unavoidable eye movements, it is hardly possible to carry out such a dynamic measurement.

However, in the examination of surfaces of other objects, such as dentures, the use of a device is known from an article by F. H. M. Jongsma e.a.. "Real-time contouring of tooth imprints", in SPIE, Vol. 492, pp. 500–506, ECOOSA 1984, in which two interference patterns are projected at an angle relative to each other by means of an interferometer. Planes which are at right angles to the bisectrix of the angle and are alternately diffusely illuminated or contain more or less highly contrasting line patterns are thereby produced in the space in which the two light beams intersect. The distance between these parallel planes is equal and depends on the angle between the light beams and the distance between the lines in the projected grating pattern. If an object is now placed in this space, it alternately intersects the diffusely illuminated planes and the planes with the images of the grating pattern. As a result of this, intersection lines become visible on the object, which lines have a constant height difference from each other, although due to the summation effect the contrast of the two intensities is very low. In order to make said height lines visible, a spatial (optical) or temporal (electronic) filtering such as that described in above article by Jongsma c.s. must therefore still be used.

A disadvantage of moiré images is that it is not possible to determine the sign of the slope other than from previous knowledge of the object. One method of overcoming this problem is described in French patent application No. 2,292,213 of 21 Nov. 1974. This patent application describes a method in which two moiré projections are compared with each other. These moiré registrations are produced in such a way that the reference plane of the second moiré registration is displaced over a distance which is smaller than half the moiré contour distance. Double contours with alternating small and larger intervals are thus produced. The contours are labelled with a colour, for example by making use of a yellow and a blue grating. The result is then a colour registration with the relatively small contour intervals yellow - blue or blue - yellow. The information of the sign of the slope is contained in the combination of distance and colour.

Another form of colour labelling is described in German patent application No. P 40 175 028 of 9 Mar. 1990. This patent application describes how two gratings of different colours are projected simultaneously on the object from different angles. The two gratings in the detection system can be processed separately by means of a colour separation mirror. The angle and the orientation of the slope relative to the sensor can then be calculated from the local spatial grating frequency on the object. What is essential in this system is the mechanical linking of the two gratings lying in one plane, so that their phase relation is fixed. As a result of this, by displacement of the gratings the noise can be averaged, while the height contours do not change position.

If unambiguous external shape information on the moist and reflecting surface of the cornea is desired, use can be made of the fluorescence technique described in the article by T. Kawara, in order to convert this reflecting surface into a Lambertian radiator. In these conditions, when there is a well-defined illumination, the local emission can then be calculated. In order to obtain a moiré contrast, use can be made of the projection technique known from an article by J. Wasowski, "Moiré topographic maps", in Opt. Communications, Vol. 2, pp. 321-323, 1970, by means of a projector of the type described by Kawara. If lasers which are suitable for this are available, it is also possible to choose the interferometer described by Wasowski as the grating producer, or another interference system can be used.

SUMMARY OF THE INVENTION

The invention aims at obviating the earlier mentioned problems in the prior art. This is realized, according to the invention, in that a system is provided for determining the topography of a curved surface, comprising a device for projecting patterns of lines on the surface to be examined, which device includes two projectors disposed at an angle relative to each other, each provided with a raster of parallel straight lines, which are positioned at right angles to the plane through the projection axes and a rectangular diaphragm, of which the long sides are parallel to the lines of the raster, and a detection device for registering the image formed on the surface, wherein the system is implemented such that an additive moiré pattern is produced and that a pilot monitor in conjunction with an electronic filter is provided for real-time visualizing this moiré pattern, and that the detection device is implemented for registering the image without moiré interference, suitable for discrete Fourier analysis.

BRIEF DESCRIPTION OF THE DRAWINGS

The invention is explained in greater detail with reference to an example of an embodiment shown diagrammatically in the drawings, in which FIG. 1 shows diagrammatically a system according to the invention;

FIG. 2 shows the projection of the intensity function on the x-axis through object c(x);

FIG. 3 shows an electronic real-time filtered viewfinder image;

FIGS. 4(a-c) respectively show a complete TV picture and the separate components from which it is composed, the first half raster and the second half raster;

DETAILED DESCRIPTION OF THE PREFERRED EMBODIMENT

Figure 7:
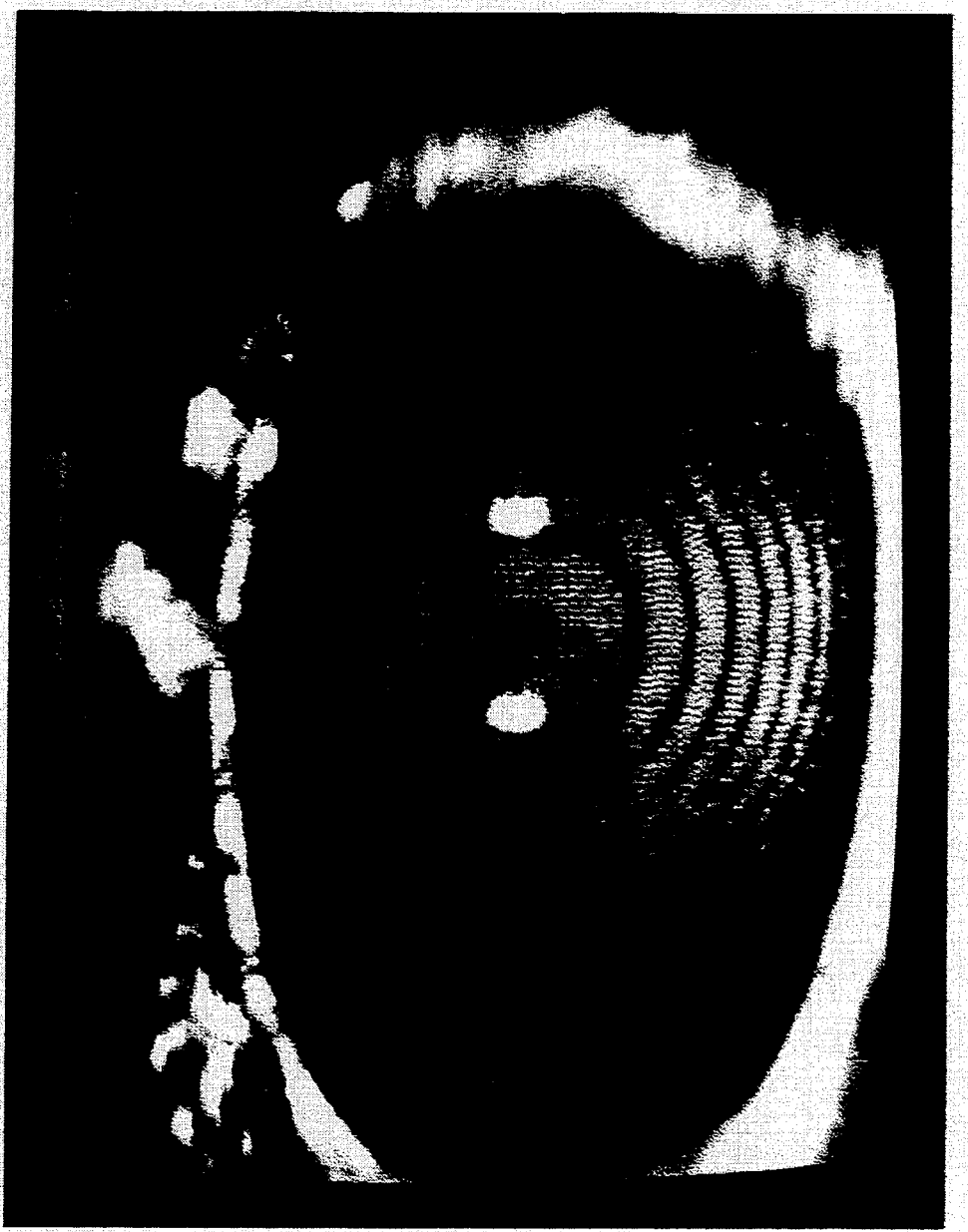

On account of the gain in sensitivity and accuracy which can be achieved with phase detection, a calculation program has been developed, in which the local phase of a projected grating on the surface to be measured is calculated relative to a reference plane at right angles to the optical axis of the sensor. Since the carrier wave itself, and not the modulation of the carrier wave, is now the basis for extracting the information, it is possible to work with relatively coarse gratings which permit correspondingly larger diaphragms. In this way it becomes possible, without causing too great a radiation load for the eye, to use a high-resolution TV camera, such as a CCD camera, which permit real-time digitising of the images through the use of a frame grabber.

The cornea to be measured is mobile and cannot be fixed, with the result that the collection time has to be very short (shorter than the integration time of a TV camera). Moreover, a part of the image can be lost through local overexposure, due to reflection on the cornea.

These problems can be solved by making use of a TV camera, like a CCD camera, and two flash tubes synchronised via a synchronizing device 13 with the camera such as is indicated in FIG. 1. The first tube is synchronised in the end of the first half raster period, and the second at the beginning of the next half raster. The total integration time is now limited to the flash times and the flash interval. Since the two flash exposures produce an independent picture independently of each other (but linked in time), one picture can supplement the information which has been lost in the other picture, for instance caused by local disturbances like undesired reflections, too strong defocussing, etc. This situation is achieved in the case of the double flash technique described, in which it is possible, for example, first to analyse the odd TV lines and then to analyse the even lines.

The system for use in the invention, as indicated in FIG. 1, comprises two projectors 3 set up at an angle with the optical axis 1 of a camera 2. Both projections contain a slide 4 containing a line pattern of about five line pairs per mm, which lines run at right angles to the plane through the projection axes. As described above, by projection of two line patterns at an angle, diffusely illuminated planes and planes with more or less highly contrasting raster images are produced alternately in the space 12 in which the two light beams cross, which images produce a height line or contour chart on intersection by an object.

The eye to be examined is treated with Na-fluorescein in Hypromellose-Bournonville ®, a substance which is also used as a replacement for natural tear moisture in the case of "dry eyes". Hypromellose serves as a solvent for Na-fluorescein. Blinking a few times causes the Na-fluorescein to be absorbed in the tear film, following which the registration can be taken.

For accurate measurements of the cornea contours, in which the liquid film must have a uniform thickness, use can be made of Healon ®, which has a low molecular weight, and in which Na-fluorescein is dissolved, as known, for example, in the case of cornea plastic with the aid of excimer lasers.

Projection lamps 5 are used as the light source in the projectors. In order to "freeze" rapid eye movements, use can be made of flash lamps 6 which are synchronised with the TV camera, and which then temporarily replace the continuous lamps in the projectors. Filters are fitted between the lamps and the slides, which filters reflect (7) the heat of the light source and reflect (8) all colours except blue-green, so that the radiation load on the eye is restricted to that of the blue-green excitation light. For projecting the grating, the projection device is provided with a projection objective 10. Placed in the focal plane of this projection objective at the side where the object lies is a rectangular diaphragm 9, of which the long sides run parallel to the lines of the grating. The aperture of the diaphragm along the narrow side is small enough to project five line pairs per mm with sufficient depth of field. The relatively large aperture of the diaphragm along the long side contributes to the desired light intensity of the height line map.

The distance setting takes place with the aid of an image, via a pilot monitor 16 on which after using an electronic analog filter 15, concentric rings appear on the cornea (FIG. 3) which cornea is imaged totally in the depth of focus of the cornea image.

A yellow-band stop filter 11 is fitted in front of the camera, which filter blocks the blue excitation light and transmits only the yellow emitted light.

The unfiltered moiré image at the location of each CCD camera contains pixel information on the spatial coordinates x, y and z. With the aid of digital image processing it is possible to make the shape of the cornea visible in detail, for example as an axial section or as a three-dimensional structure. In order to obtain both a high axial and a high lateral resolution, the ring pattern such as that obtained after electronic analog filtering is not used as the starting point, but instead the unfiltered TV picture is analysed TV line by line.

As soon as the instrument is set, a frame grabber 14 sees to the digitisation and the transmission of the signal to the monitor 18 coupled to a computer 17. There the signal is analysed line by line (FIG. 4). This takes place both for the left-hand projection and for the right-hand projection in the calculation, possibly simultaneously. In this way any missing information in one image can be supplemented through the other image. This also applies to defocussing effects, which in the case of the two projections are left-right opposed.

One method for analysing signals is to use Fourier analysis. A condition for this analysis is that the signal is not overmodulated, as is unavoidable in the case of a moiré contrast. The TV pictures registered can be regarded as being phase-modulated, the height of the object to be measured being modulated in the phase of the projected grating.

FIG. 2 shows in a one-dimensional manner how the grating is modulated and projected, in which:

a(x) = perpendicular line of p(x) through the origin

{Z(x)} = collection of perpendicular lines of p(x) with as intersection point with c(x): $\beta$ $\phi$ = projection angle p(x) = intensity function axis with O as origin $\alpha$ = distance between a(x) and any line of Z(x) representing the original phase angle produced by the raster $\beta$ = abscis value of the intersection point with c(x) representing the phase angle which comes about after projection The diaphragm setting, passes the first and zeroth order, with the result that the intensity can be characterised by:

$$i(\alpha) = A \sin(\omega_o \cdot \alpha) + d \qquad (1)$$

where:

$\omega_o$: raster function

A: amplitude d: D.C. shift

The projected modulated wave form then acquires a shape of the type:

$$i(\beta) = A \sin[\omega_o\{\cos(\phi)\cdot\beta + \sin(\phi)\cdot c(\beta)\}]\cdot d \qquad (2)$$

where:

c($\beta$) = height of the object written as function, $\Psi$ = projection angle.

Note that i($\beta$) is the image measured with the camera. The phase, thus the height of the object, can be reconstructed from the modulated wave form i($\beta$) by means of the Fourier transform. In principle, the following steps are necessary to reconstruct the height:

$$I(\omega) = F\{i(\beta)\} \qquad (3)$$

$$Y(\omega) = D\{I(\omega)\} \qquad (4)$$

$$y(\beta) = F^{-1}\{Y(\omega)\} \qquad (5)$$

$$T\cdot c(\beta) = arg(y(\beta)) \wedge T\cdot c(\beta) + k\pi = T\cdot c(\beta) \, k\epsilon Z \qquad (6)$$

where:

T: constant factor

F{ }: forward Fourier transform $F^{-1}${ }:backward Fourier transform

D{ }: demodulation transform arg( ): argument/phase of a complex number/series k: constant, element of Z A data processing system will carry out these operations in discrete form. For the discrete Fourier transform there is a very suitable method which reduces the number of calculations required. This is the so-called Fast Fourier Transform (FFT). In analogy to the one-dimensional analysis technique described, there is the possibility of carrying out a two-dimensional analysis. Since the two-dimensional Fourier transform comprises two one-dimensional transforms which can be carried out independently of each other, the same method as that mentioned in formula (3), (4), (5) and (6) applies.

For determining radii of curvature of a demodulated image it is possible to use, inter alia, elliptical or polynomial curve fitting. A method for this is, for example, Gaussian elimination. Eccentricity, astigmatism and the like can be determined or calculated from these fittings. The determination of fittings can also be carried out in a one-dimensional or a two-dimensional manner. For both transform technique and fitting technique the two-dimensional method is more accurate, because in principle all measured image points are brought into relation with each other, which corresponds to reality. Measuring errors are also averaged out more effectively or are even eliminated in this way. In order to achieve further improvements, digital filter techniques will be required.

Figure 5:
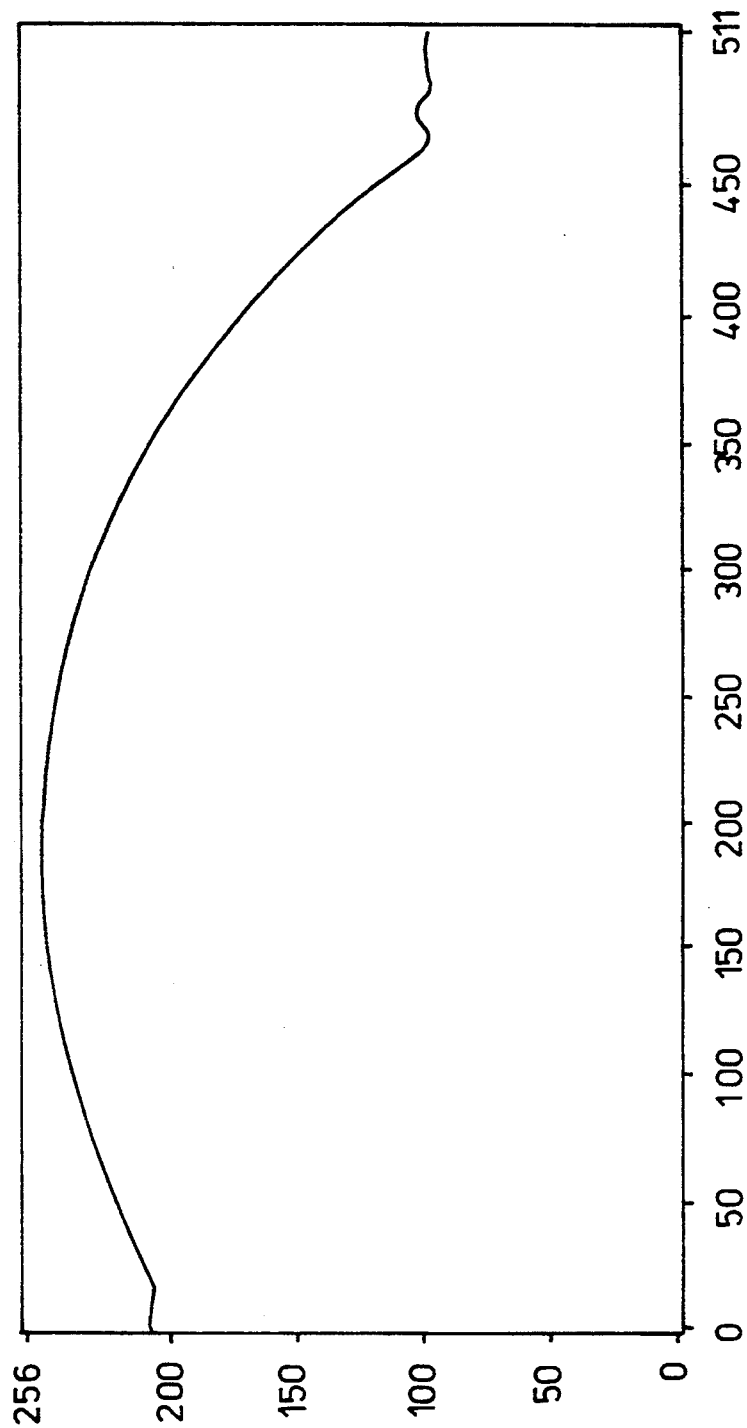
FIG. 5 shows a digitally obtained phase reconstruction of a TV line.
Figure 6:
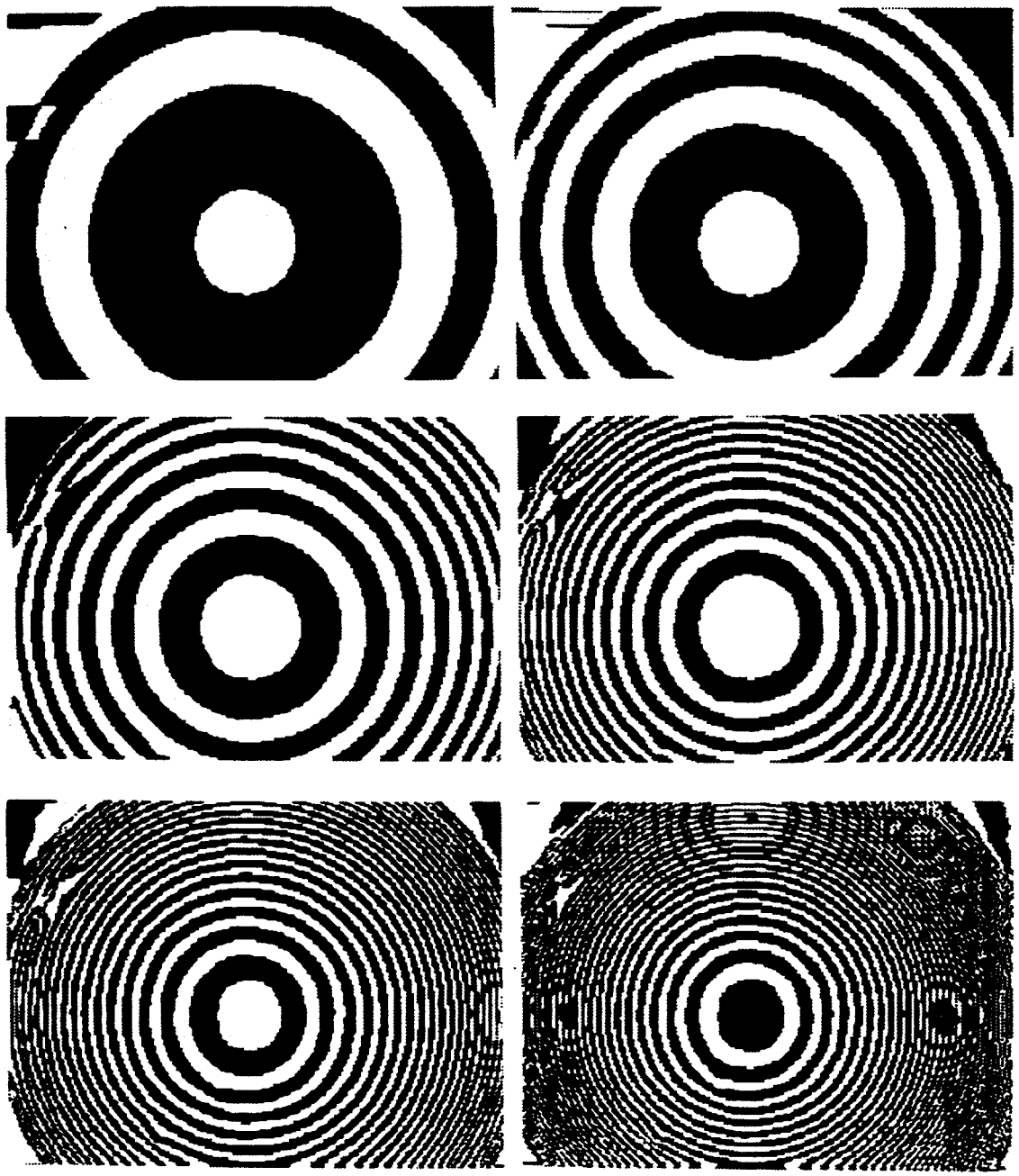
FIG. 6 shows a 2-D reconstruction of a half TV raster of a spherical surface.

For an example of above processing reference is made to FIGS. 5 and 6, in which a digitally obtained phase reconstruction of a (pilot) monitor line (projection on a spherical surface) and a two-dimensional reconstruction of a half raster of a spherical surface are respectively shown. The contours, processed in FIG. 6, can be adjusted afterwards with intervals as desired. Details, such as a defect in the model (shown at top left in FIG. 6) can thus be visualized.

In the above explained technique the lateral horizontal resolution is determined by the band width of the TV system or by the resolution of the frame grabber, and no longer by the fringes of the moiré pattern, which as a beat pattern by definition have a much lower lateral resolution. The vertical resolution is determined by the number of TV lines. Apart from being used as a keratometer, on account of the absence of the need for having previous knowledge of the object to determine the sign of the slope, the system can also be made suitable for determining the three-dimensional shape of other objects such as contact lenses, dentures, models and industrial objects. Advantageously, the system can be used such that by means of digital processing of the height contours already calculated the requested information for, for example, an optician, contact lens specialist, ophthalmologist or technician becomes available.

The system according to the invention can be used for determining a curved surface, in which an accurate height line or contour pattern with a high lateral resolution is the basis for obtaining the required data, as needed, for example, for fitting contact lenses or for surgery in the ocular media. When the system is used as a keratometer, a height line map can be created on the cornea, comprising the whole cornea, and the detection device will also be designed in such a way that the whole height line map is available in real time in digital form for further data processing, with the result that an accurate determination of the central and peripheral curvature of the cornea becomes possible.

This is obtained through the fact that the above system includes a projection device provided with two projectors disposed at an angle relative to each other, each positioned at right angles to the plane through the projection axes and a rectangular diaphragm, of which the long sides are parallel to the lines of the grating.

Through the use of these projectors, diffusely illuminated planes and planes with more or less highly contrasting grating images can be obtained, which when intersected by an object produce a highly contrasting moiré contour or height line map after analog or digital processing of the signal.

A radiation load which is acceptable for the eye to be examined will be produced by making use of a relatively large diaphragm aperture from the detector side, even when using the required blue-green excitation light.

The angle at which projection takes place depends on the slope or curvature of the surface to be examined.

Through the nature of the data processing, considerably larger projection angles are possible than in the case of direct formation of moiré images, while the sensitivity gain compared with respect to the direct moiré system also makes very small angles effective. In the case of the keratometer a real-time moiré image is created by means of an analog electronic filter, for a setting and viewfinder image or monitor 18.

In addition, in particular in the case of keratometers, the light source used for the viewfinder image is a lamp with slit shaped filament or slit shaped gas discharge, which is projected in vertical orientation on the vertical slit-shaped diaphragm of the projector. In order to minimise the thermal load of the projection device and in order to keep the light load of the eye low, relatively coarse gratings are projected, which gratings can still be projected with sufficient depth of field when the diaphragm aperture is large. The detection device can be embodied such that the definition of the height line map takes only a short time, with the result that possible movements of the eye during the exposure do not adversely affect the quality of the registration.

Through specular reflections of the surface of the object, differences can occur in the intensities of the two grating images, with the result that the derivation of the phase height of the gratings from the local intensity is jeopardised, and so also is the formation of the height line map.

Providing the object with a fluorescent layer prevents specular reflections in the case of this method. Use is made of a continuous light source which radiates light with a wavelength which causes emission in a fluorescent substance applied to the object. A substance which is suitable for this is Na-fluorescein, of which the optimum excitation wavelength, depending on the solvent, is 460 to 510 nm (blue-green) and the emission wavelength is 520–560 nm (yellow). The projection device is fitted with a filter which transmits only light of the excitation wavelength, and in the detection system there is a filter which transmits only light of the emission wavelength. The interfering influences as the result of reflections of the excitation light are removed through this latter filter. In the case of the keratometer embodiment, the viewing axis and optical axis of the keratometer can be aligned as follows. The person to be examined is asked to fix the eye on a light source, the optical axis of which coincides with the optical axis of the instrument. The operator of the keratometer ensures then that this light source reflected by the eye goes into the centre of the image.

What is claimed is:

1. A system for determining the topography of a curved surface, comprising a projection device means for projecting patterns of lines on the surface, the projection device means including two independent light projectors disposed at an angle relative to each other, each projector having a projection axis and including a grating having parallel straight lines, wherein each grating is positioned at a right angle to the projection axis of its respective projector, a rectangular diaphragm having the long sides parallel to the lines of the grating, a detection device means for registering an image formed on the surface and a flash light source synchronized in sequence with the detection device means, wherein the detection device means comprises a frame grabber means for separately registering a projected grating of each projector in said sequence for explicit digital image analysis to obtain the topography of the curved surface.

2. A system according to claim 1, wherein the detection device means comprises a TV-camera and a synchronizer means for triggering the flash light source of the first projector at the end of a first half raster period and for triggering the flash light source of the second projector at the beginning of a second half raster period, the flash light sources illuminating a complete TV-raster wherein the half rasters are adapted to complement each other.

3. A system according to claim 2, wherein the detection device means further comprises a data processor means for analyzing the image to obtain a height function according to Fourier transform, demodulation, and inverse Fourier transform, on one or more half rasters simultaneously in a one or two dimensional manner for reconstructing the topography.

4. A system according to claim 3, wherein the projectors are angled to cause the projected gratings to intersect on the curved surface, wherein the frame grabber is capable of distinguishing the intersecting gratings and separately registering the gratings for individual digital analysis via the data processor means.

5. A system according to claim 1, wherein each light projector further comprises a continuous light source, wherein both the continuous and flash light sources are slit shaped such that the continuous light and flash light sources are projected from the projectors in a vertical orientation through the rectangular diaphragm.

6. A system according to claim 5, wherein the detection device means comprises an analog contrast filter and a pilot monitor, whereby the analog filter emphasizes additive height contours in real time on a topography image which is displayed on the pilot monitor.

7. A system according to claim 1, wherein the projectors of the projection device means are each disposed at an angle ranging from 10° to 45°.

8. A system according to claim 1, wherein each projector comprises a grating projecting objective, the rectangular diaphragm being placed in a focal plane of the objective.

* * * * *